United States Patent
Phua et al.

(10) Patent No.: US 8,246,547 B2
(45) Date of Patent: Aug. 21, 2012

(54) PACKAGES OF APPARATUS FOR NON-INVASIVE DETECTION OF PULSE RATE AND BLOOD FLOW ANOMALIES

(75) Inventors: Chee Teck Phua, Singapore (SG); Chin Leng Peter Lim, Singapore (SG); Boon Chong Gooi, Singapore (SG)

(73) Assignee: Nanyang Polytechnic, Singapore (SG)

( * ) Notice: Subject to any disclaimer, the term of this patent is extended or adjusted under 35 U.S.C. 154(b) by 425 days.

(21) Appl. No.: 12/440,587

(22) PCT Filed: Jun. 27, 2007

(86) PCT No.: PCT/SG2007/000180
§ 371 (c)(1),
(2), (4) Date: Mar. 9, 2009

(87) PCT Pub. No.: WO2008/033099
PCT Pub. Date: Mar. 20, 2008

(65) Prior Publication Data
US 2010/0042006 A1   Feb. 18, 2010

(30) Foreign Application Priority Data
Sep. 15, 2006  (SG) .................. 200606459

(51) Int. Cl.
*A61B 5/02* (2006.01)
(52) U.S. Cl. ........................ 600/500; 600/504
(58) Field of Classification Search .......... 600/500, 600/504, 505–509, 407, 409, 419
See application file for complete search history.

(56) References Cited

U.S. PATENT DOCUMENTS

| | | | | |
|---|---|---|---|---|
| 2,149,847 A * | 3/1939 | Kolin | .................. | 73/861.13 |
| 4,202,350 A * | 5/1980 | Walton | .................. | 600/503 |
| 4,881,413 A * | 11/1989 | Georgi et al. | .............. | 73/861.12 |
| 5,794,622 A * | 8/1998 | Chopp et al. | .................. | 600/431 |
| 5,873,837 A * | 2/1999 | Lieber et al. | .................. | 600/504 |
| 5,935,077 A * | 8/1999 | Ogle | .................. | 73/861.12 |
| 6,669,648 B1 * | 12/2003 | Fortin et al. | .................. | 600/490 |
| 6,856,832 B1 * | 2/2005 | Matsumura et al. | .......... | 600/523 |
| 6,910,382 B2 * | 6/2005 | Tang et al. | .................. | 73/722 |
| 7,463,028 B2 * | 12/2008 | Dietz et al. | .................. | 324/318 |
| 2003/0016010 A1 * | 1/2003 | Kandori et al. | .............. | 324/248 |
| 2004/0066674 A1 * | 4/2004 | Tang et al. | .................. | 365/200 |
| 2004/0162477 A1 * | 8/2004 | Okamura et al. | .............. | 600/409 |
| 2005/0038345 A1 * | 2/2005 | Gorgenberg et al. | ......... | 600/485 |
| 2005/0054939 A1 * | 3/2005 | Ben-Ari et al. | .............. | 600/506 |
| 2005/0197523 A1 * | 9/2005 | Chung et al. | .................. | 600/15 |
| 2006/0001512 A1 * | 1/2006 | Garcia et al. | .................. | 335/205 |
| 2006/0194327 A1 * | 8/2006 | Kahlan et al. | .................. | 436/86 |

FOREIGN PATENT DOCUMENTS

WO   WO 2004/028361   *   4/2004

OTHER PUBLICATIONS

Tenforde TS (2005) Magnetically induced electric fields and currents in the circulatory system. Prog Biophys Mol Biol 87:279-288.*

* cited by examiner

*Primary Examiner* — Navin Natnithithadha
*Assistant Examiner* — Sunita Reddy
(74) *Attorney, Agent, or Firm* — Pyprus Pte Ltd

(57) ABSTRACT

The present invention provides a package for an apparatus for non-invasively monitoring of blood flow of an object, a magnetic field sensing device, and a magnetic source positioning device.

15 Claims, 7 Drawing Sheets

(a)

(b)

(c)

PACKAGES OF APPARATUS FOR NON-INVASIVE DETECTION OF PULSE RATE AND BLOOD FLOW ANOMALIES

FIELD OF THE INVENTION

The present invention generally relates to apparatuses for monitoring blood flows, and more particularly to packages of an apparatus for non-invasive detection of pulse rate and blood flow anomalies.

BACKGROUND OF THE INVENTION

With the advancement of bioelectronics, portable health monitoring devices are getting popular for they are able to provide continuous monitoring of an individual's health condition with ease of use and comfort. The portable health monitoring devices are increasingly used at places such as home, ambulance and hospital, and at situations including military training and sports.

Pulse rate and blood flow characteristics are important parameters subject to continuous monitoring because they are important in assessing the health condition of an individual. Healthcare institutes such as the hospitals and elderly care centers can use this information to remotely monitor the health conditions of their patients. This is particularly important for paraplegic patients whose blood flow anomalies need to be detected early. In addition, blood flow anomaly monitoring for patients after major surgeries is important to ensure patients' smooth recovery.

Furthermore, pulse rate and blood flow information of individuals subjected to crowded and cramped conditions with limited physical activity may be utilized to trigger alert for immediate attention when blood flow anomalies, such as deep vein thrombosis, are detected. Similar monitoring and alert system may also be deployed during disaster where life condition of the affected personnel can be assessed continuously for rescue risk management. Finally, it is important for monitoring of the pulse rate and blood flow of personnel working in dangerous environments such as deep sea condition (divers), high temperature (fire-fighters), and deep underground (coal miners).

Current apparatuses for non-invasive measurements of blood pulse rate use electrical, mechanical and optical means for sensing. The apparatuses can come in the form of chest stripes, socks attachments, wrist-watches, and finger attachments. However, each of the apparatuses for blood pulse measurement has its weaknesses. Chest stripes and sock attachments usually measure the body electrical signals to determine the pulse rate; it is simple but requires the use of complex algorithms and/or reference signals to reduce noise due to motion artifacts. Measurement of pulse rate by mechanical means employs the detection of pulsation on the skin, which is highly susceptible to other motion artifacts. Optical means for pulse rate measurements usually come as finger attachment device. Such device employs the use of special light sources and detectors, which normally results in higher power consumption. With the various apparatuses discussed above, it is important to note that most of these apparatuses are not able to acquire information on blood flow.

Another type of apparatuses for measuring pulse rate and blood flow employs non-invasive electromagnetic method. For example, U.S. Pat. No. 5,935,077 discloses an electromagnetic blood flow sensor that uses a bipolar magnetic field source to provide a varying magnetic field with a component parallel to the skin and through the blood vessel, a single sense electrode on the skin adjacent to the blood vessel, a reference electrode, and a detector that samples the sense electrode signal in synchronism to the varying magnetic field. However, the non-invasive electromagnetic apparatuses using electrodes to measure pulse rate and blood flow have poor signal-to-noise ratios as most of the systems employ electrodes; the apparatuses are more susceptible to body electrical noise and motion artifacts. In addition, most of these apparatuses employ the reversal of magnetic field polarity to achieve signal acquisition of pulse rate and blood flow information. This method usually requires the use of an electromagnet, which will result in high power consumption. As such, the current electromagnetic apparatuses of pulse rate and blood flow monitoring are not portable and are not meant for ambulatory use.

The inventors of the present invention have previously discovered a magnetic method for non-invasive detection blood pulse rate and flow anomalies without the need of direct contact between sensor and skin. See, Singapore patent application No. 200601301-5, titled "Apparatus and method for non-invasively sensing pulse rate and blood flow anomalies" which is incorporated herein for its entirety. The magnetic method has many advantages over other non-invasive methods. For example, the other non-invasive methods acquire their signals by deforming the blood vessels. The deformation of blood vessels could be achieved by for example the use of a gaseous device as disclosed in U.S. Pat. App. No. 2004/0010199 A1. In contrast, the magnetic method does not need any deformation of blood vessels for signal acquisition.

SUMMARY OF THE INVENTION

One embodiment of the present invention provides a package for an apparatus for non-invasively monitoring of blood flow of an object. The package comprises a magnetic source for producing a localized, uni-directional, and constant magnetic field; a signal acquisition module with a magnetic sensor disposed within the magnetic field for detecting the modulations of the magnetic field caused by the blood flow; and a gaseous damping cushion, wherein the magnetic source may be disposed within or onto the gaseous damping cushion; thereby the gaseous damping cushion enables the modulations of the magnetic field of the magnetic source caused by the blood flow to be amplified and/or propagated, and isolated from external noises.

In another embodiment of the package, the package further comprises a signal conditioning module for converting the output of the signal acquisition module with appropriate amplifications; and a digital signal processing module for processing the output signal from the signal conditioning module; thereby pulse rate and blood flow anomaly can be monitored.

In another embodiment of the package, the package further comprises a display/user interface/alarm module for providing visual or acoustic notification to a user. In other embodiments of the package, the magnetic source is a permanent magnet or an electromagnet or a plurality of electromagnets. In a further embodiment, the strength of the magnetic field produced by the plurality of electromagnets is controlled electronically.

In another embodiment of the package, the magnetic sensor is any magnetic sensor with appropriate sensitivity of detecting the modulation of the magnetic field from the magnetic source. In further embodiments of the package, the magnetic sensor is a giant magnetoresistance (GMR) magnetic sensor, a tunneling magnetoresistive (TMR) based magnetic sensor, or an anisotropic magnetoresistive (AMR) sensor.

In another embodiment of the package, the signal acquisition module comprises a printed circuit board and two magnetic sensors; wherein the printed circuit board is sandwiched by the two magnetic sensors; and wherein the two magnetic sensors are configured to have an orthogonal formation.

In another embodiment of the package, the gaseous damping cushion has a doughnut configuration with a circular chamber; wherein the circular chamber is disposed with means for allowing the embedded magnetic source to move and holding the embedded magnetic source in place. In a further embodiment, the means within the circular chamber comprises a plurality of semi-flexible flaps. In yet another embodiment of the package, the gaseous damping cushion comprises air or non-magnetic gas.

Another embodiment of the present invention provides a magnetic field sensing device. The magnetic field sensing device comprises two magnetic sensors for sensing a magnetic field; a printed circuit board, wherein the printed circuit board is sandwiched by the two magnetic sensors that are configured to have an orthogonal formation, and wherein the two magnetic sensors are electrically coupled to the printed circuit board; thereby the signals from the two magnetic sensors are outputted into the printed circuit board; and a means for channeling the signals from the printed circuit board so that the signals can be processed.

In another embodiment of the magnetic field sensing device the magnetic sensors are any magnetic sensor with appropriate sensitivity of detecting the modulation of the magnetic field from the magnetic source. In further embodiments, the magnetic sensor is a giant magnetoresistance (GMR) magnetic sensor, a tunneling magnetoresistive (TMR) based magnetic sensor, or an anisotropic magnetoresistive (AMR) sensor.

Another embodiment of the present invention provides a magnetic source positioning device. The magnetic source positioning device comprises at least one magnetic source; and a gaseous damping cushion that has a doughnut configuration with a circular chamber; wherein when the at least one magnetic source is embedded within the circular chamber, the circular chamber is disposed with means for allowing the embedded magnetic source to move and positioning the embedded magnetic source within the circular chamber.

In another embodiment of the magnetic source positioning device, the magnetic source is a permanent magnet or an electromagnet.

In another embodiment of the magnetic source positioning device, the means within the circular chamber comprises a plurality of semi-flexible flaps. In yet another embodiment of the magnetic source positioning device, the gaseous damping cushion comprises air or non-magnetic gas.

The feature of gaseous damping cushion embedded with the magnet source provides the package of the present invention with a few advantages. For example, it allows the magnet source to be positioned along the physical feature of the skin with good conformity and yet not deforms the physical feature topology on the measurement site. It enables peripheral mounting without the need for a rigid structure to house the gaseous damping cushion and magnetic source. It also improves the probability of detection via amplification and propagation of the source signal.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the Figures, in which like reference numerals denote like elements.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

In the following detailed description, specific details are set forth in order to provide a thorough understanding of the invention. However, it will be understood by those skilled in the relevant art that the present invention may be practiced without these specific details. In other instances, well-known methods, procedures, components, and materials have not been described in detail so as not to obscure the present invention.

As mentioned above, the inventors of the present invention have previously discovered that when a localized, uni-directional, and constant magnetic field is applied to a blood vessel, the flow of pulsatile blood can modulate the applied magnetic field and that the modulation of the magnetic field can be sensed directly if a magnetic sensor is disposed in a suitable position within the magnetic field. An earlier filed Singapore patent application No. 200601301-5 has disclosed a non-invasive magnetic apparatus and method for non-invasively sensing pulse rate and blood flow in an object including human. This Singapore patent application is incorporated herein in its entirety.

Figure 1:
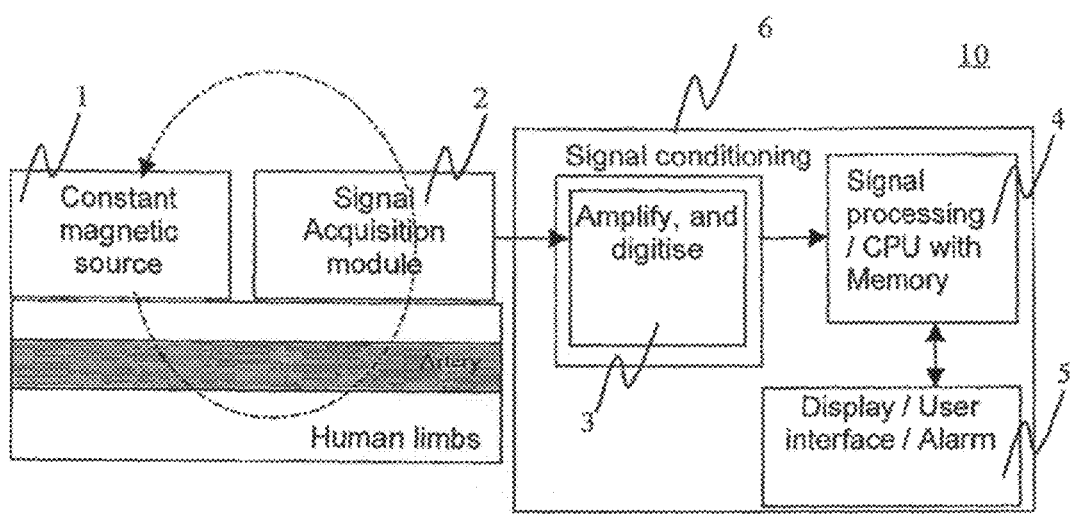
FIG. 1 is a functional block diagram of a known non-invasive magnetic apparatus for sensing pulse rate and blood flow in an object.

In order to better understand the present invention, the relevant parts of the non-invasive magnetic apparatus disclosed in Singapore patent application No. 200601301-5 will be briefly described hereinafter. Briefly, the non-invasive magnetic apparatus comprises a magnetic source for providing the magnetic field, a magnetic sensor for acquiring the signals of modulation, and a signal processing/displaying subunit for processing and outputting the processed signal. As shown in FIG. 1, the non-invasive magnetic apparatus 10 comprises a magnetic source 1, a signal acquisition module 2, and a signal processing/displaying subunit 6 including a signal conditioning module 3, a signal processing module 4, and a display/user interface/alarm module 5. The magnetic source 1 provides a localized, uni-directional, and constant magnetic field that is close to a major blood vessel. The flow of pulsatile blood in the artery modulates the applied magnetic field to create a modulated magnetic signature of blood flow (MMSB). The MMSB is translated by the signal acquisition module 2 to an electrical signal, which is then conditioned and digitized for signal processing. Then, the processed signal, primarily the pulse rate and blood flow profile, will be sent to the display/user interface/alarm module.

The signal acquisition module 2 comprises a magnetic sensor that is able to translate magnetic variations to voltages proportional to the variations of the magnetic signature. The magnetic sensors suitable for the present invention include, but are not limited to, spintronics based sensors (e.g. giant magnetoresistive (GMR) sensor and tunneling magnetoresistive (TMR) sensor), anisotropic magnetoresistive (AMR) sensors and any magnetic based sensors. One exemplary magnetic sensor is a Spintronics based magnetic sensor (e.g., AAH002-02 manufactured by NVE Corporation). It is to be noted that other magnetic-based sensors with different sensitivities may also be used to detect the modulated magnetic signature of blood flow (MMSB), but the related parameters (e.g., the strength of the magnetic source, the distance between the magnetic source and sensor, and the relative placement and orientation of the magnetic source and sensor with respect to a blood vessel) will have to be modified with appropriate support from experimental results.

Figure 2:
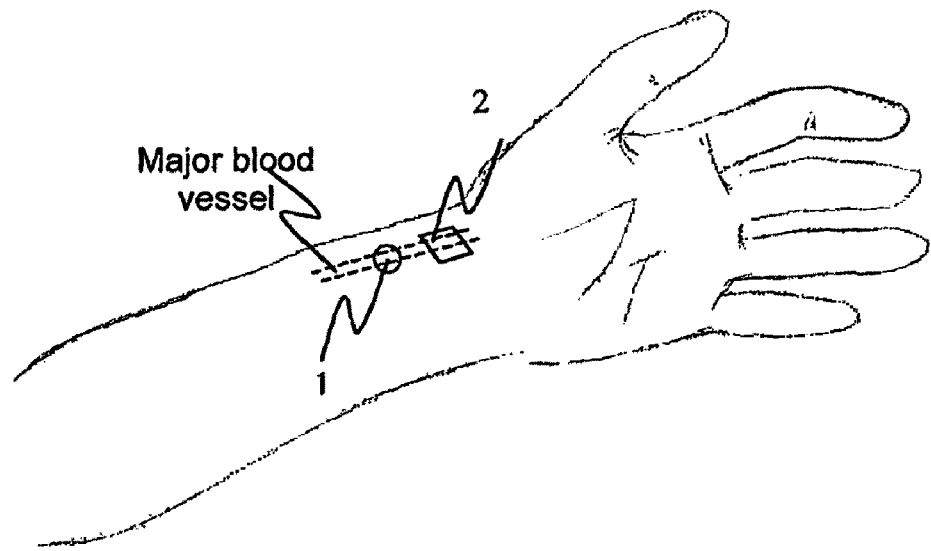
FIG. 2 shows a top view of hand with the known non-invasive magnetic apparatus.
Figure 3:
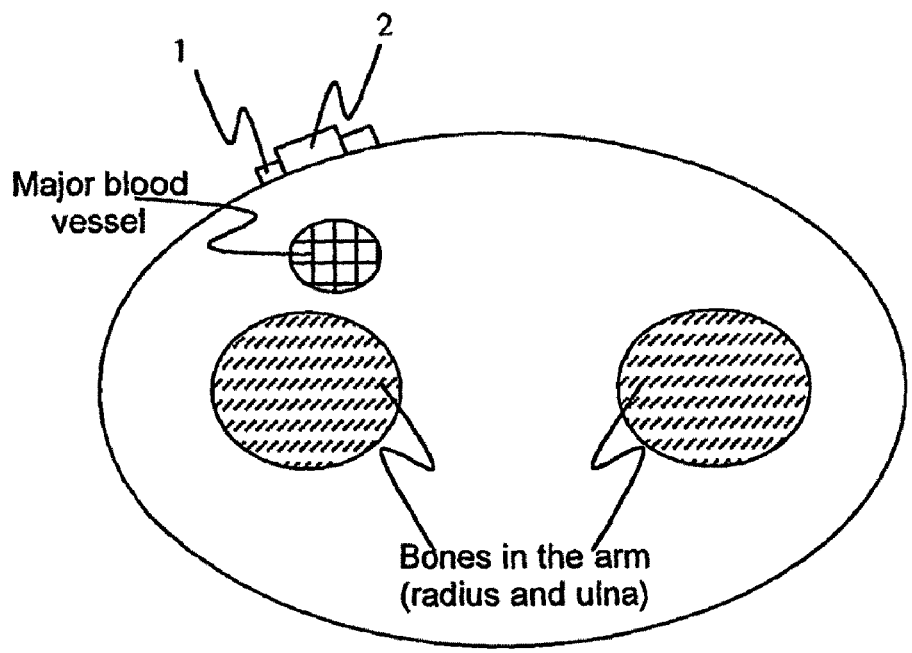
FIG. 3 shows a cross-section view of hand with the known non-invasive magnetic apparatus.

As shown in FIGS. 2 and 3, the non-invasive magnetic apparatus could be a wrist-wearing device where the magnetic source 1 and the magnetic sensor 2 are positioned relatively to the blood vessel. The processed signals, named modulated magnetic signature of blood (MMSB), are a function of the strength of the magnetic source, the sensitivity of the sensor, the distance between them, and their relative placement and orientation with respect to a major blood vessel near the surface of the skin. For any given apparatus, the strength of the magnetic source and the sensitivity of the magnetic sensor are specified; they are not subject to subsequent manipulation once they are manufactured. It is to be noted that when electromagnetic components are used as magnetic sources their magnetic strengths can be operably controlled. However, the MMSB can still be enhanced by providing the freedom to the apparatus, where the freedom would enable the user to freely adjust the magnetic source/sensor in terms of their relative placement and orientation so as to acquire the MMSB better. In addition, it would be desirable to enhance the MMSB by other means without changing the strength of the magnetic source and the sensitivity of the magnetic sensor. Furthermore, the non-invasive magnetic apparatus as a long monitoring device needs to provide comfort to the wearers.

Figure 4:
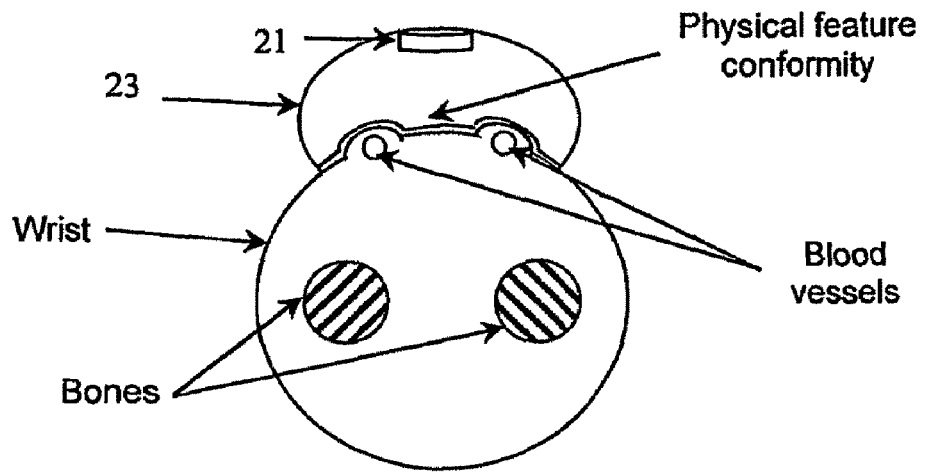
FIG. 4 shows a cross-sectional view of the package for a non-invasive magnetic apparatus in accordance with one embodiment of the present invention.

Now referring to FIG. 4, there is provided a cross-sectional view of the package for a non-invasive magnetic apparatus in accordance with one embodiment of the present invention. The package for a non-invasive magnetic apparatus 20 comprises a magnetic source 21, a magnetic sensor 22 (not shown here), and a gaseous damping cushion 23. The means for holding the package 20 is not shown herein in order not to obscure the principles of the present invention. Any known means or methods for holding a wrist/limb wearing device would be suitable for the package 20 of the present invention. The cross section of the limb is shown here is to show that the gaseous cushion 23 provides good physical feature conformity. It is to be noted that the description of packages in this application does not include all components that may be included in the packages; instead, only the magnetic source and sensor are used to illustrate the principles of the present invention. The inclusion of other components into the packages of the present invention would be evident to those skilled in art without any undue experiments.

The magnetic source may be any suitable means that is capable of producing constant magnetic field. The constant magnetic source may be permanent magnet, coil of wire, coil of wire on a ferromagnetic material, or coil of wire on a magnet. The magnetic sensor has been discussed above. The gaseous damping cushion comprises air or non-magnetic gas.

Figure 5:
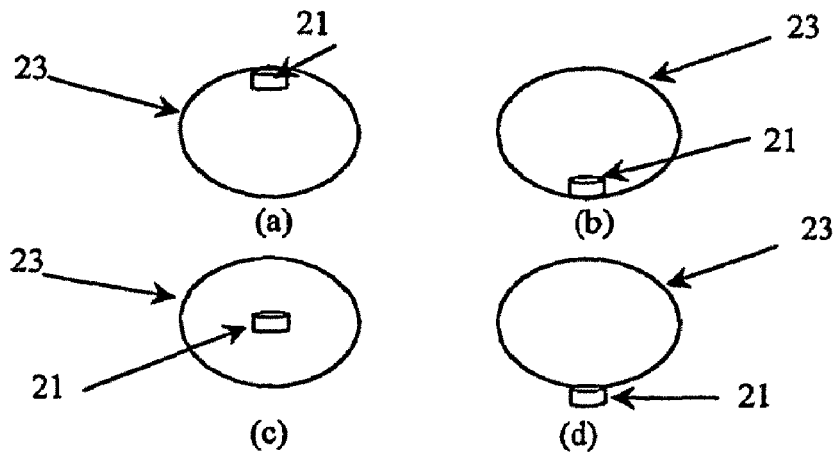
FIG. 5 shows four exemplary configurations of the magnetic source and the gaseous damping cushion.

The position of the magnetic source can be mounted variably in relation to the gaseous damping cushion. As shown in FIG. 5, there are provided four exemplary configurations of the magnetic source and the gaseous damping cushion: (a) the magnetic source is mounted on the top (interior) of the gaseous damping cushion; (b) the magnetic source is mounted at the bottom of the gaseous damping cushion; (c) the magnetic source is freely floating within the gaseous damping cushion; and (d) the magnetic source is mounted onto the bottom (exterior) of the gaseous damping cushion.

Figure 6:
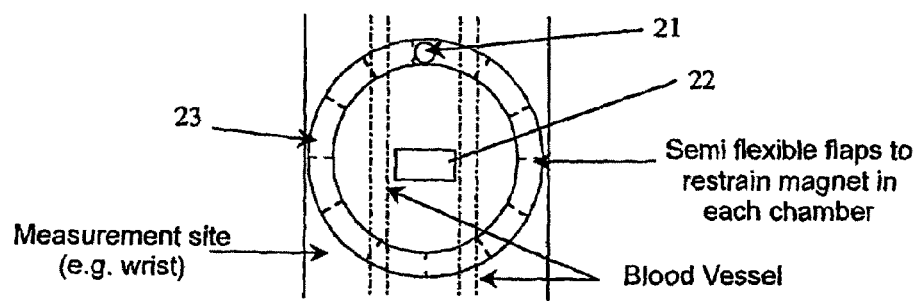
FIG. 6 shows a plan view of the package for a non-invasive magnetic apparatus in accordance with another embodiment of the present invention.

Now referring to FIG. 6, there is provided a plan view of the package for a non-invasive magnetic apparatus in accordance with another embodiment of the present invention. The gaseous damping cushion 23 has a doughnut shaped configuration. It further comprises means that allow the magnetic source to be movable along the circular chamber but restrain the magnetic source at a certain position after the user decides not to move it anymore. In one embodiment as shown in FIG. 6, the means for controlling the movement and position of the magnetic source within the circular chamber comprises a plurality of semi-flexible flaps distributed within the circular chamber. The semi-flexible flaps allow the magnetic source to be movable within the circular chamber and at the same time have the ability to hold the magnetic source in its position. The package 20 may further comprises a printed circuit board (not shown in FIG. 6), where the printed circuit board is designed to be mounted with at least one magnetic sensor which is able to detect magnetic field in any direction.

The movement ability of the magnetic source afforded by the gaseous damping cushion enables the user to avoid the saturation of the magnetic sensor. This is important as individuals have different physical features on the various blood pulse signal acquisition sites.

Figure 7:
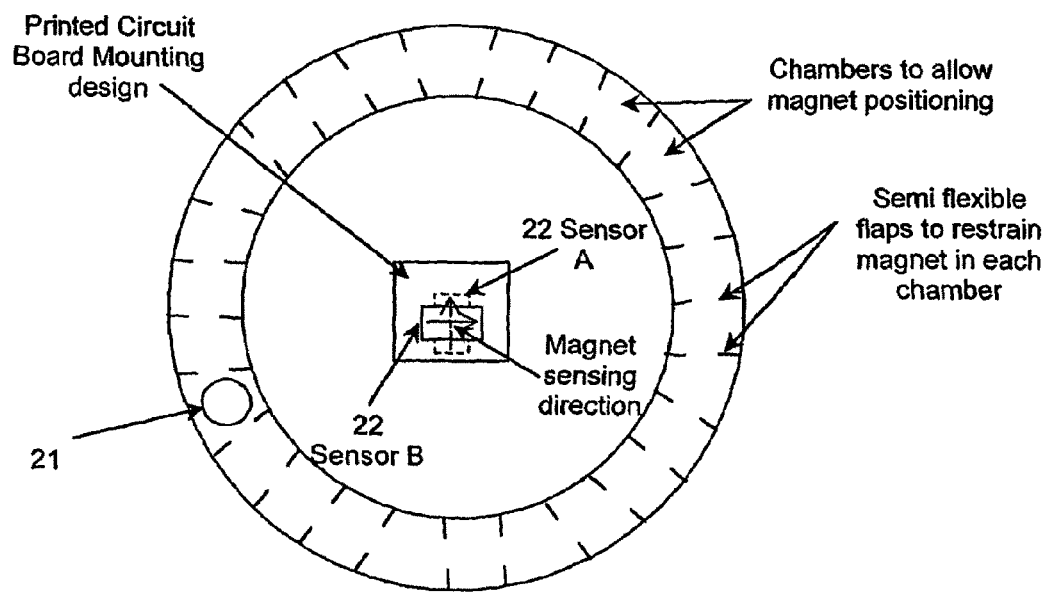
FIG. 7 shows a plan view of the package for a non-invasive magnetic apparatus in accordance with another embodiment of the present invention.

Referring to FIG. 7, there is provided a plan view of the package for a non-invasive magnetic apparatus in accordance with another embodiment of the present invention. The package is different from the one shown in FIG. 6 in that it comprises a printed circuit board and two magnetic sensors where the two magnetic sensors are orthogonally mounted onto the printed circuit board with appropriate connectivity.

Figure 8:
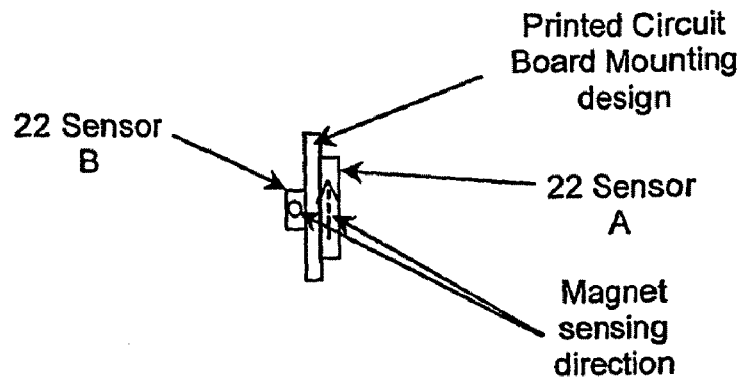
FIG. 8 shows a side-view of the printed circuit board and two magnetic sensors in accordance with one embodiment of the present invention.

Referring to FIG. 8, there is provided a side-view of the printed circuit board and two magnetic sensors in accordance with one embodiment of the present invention. As shown in FIG. 8, the printed circuit board is sandwiched by two magnetic sensors where the directions of the two sensors are in orthogonal formation. The orthogonal formation enables the magnetic sensors to detect magnetic fields without adjusting the directions of the magnetic sensors, making it an omni-magnetic sensing device. The printed circuit board is electronically coupled with the magnetic sensors so that it can acquire the magnetic field signals from the magnetic sensors and output the acquired signals to a signal processing component that is electronically coupled with the printed circuit board. While this magnetic field sensing device has been described in the context of acquiring MMSB signals, it can be used in any suitable application for detecting magnetic field.

Figure 9:
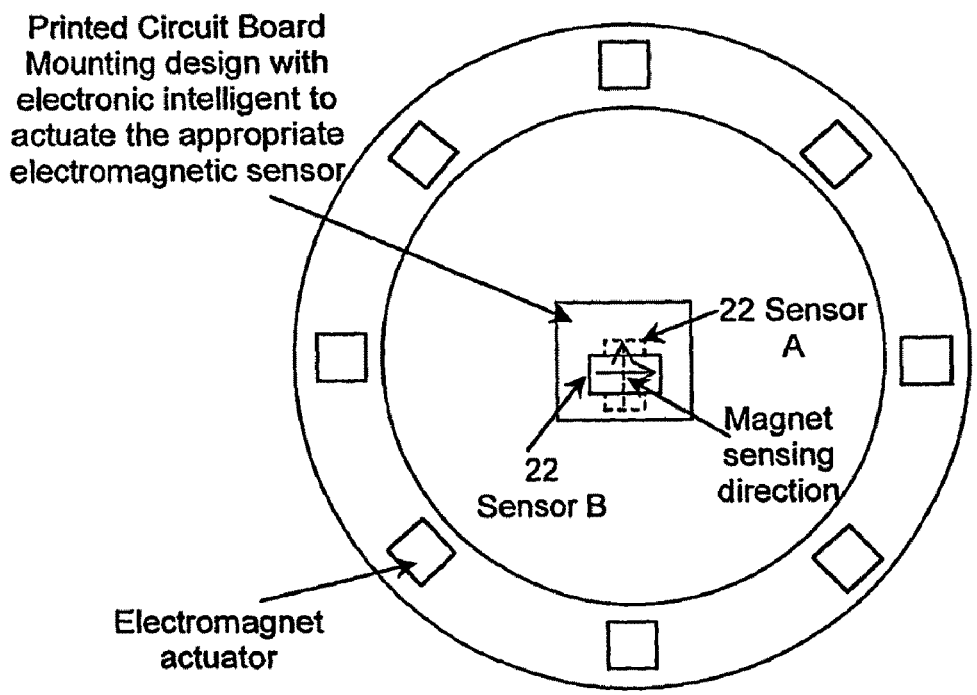
FIG. 9 shows a plan view of the package for a non-invasive magnetic apparatus in accordance with another embodiment of the present invention.

Referring now to FIG. 9, there is provided a plan view of the package for a non-invasive magnetic apparatus in accordance with another embodiment of the present invention. The package comprises a plurality of electromagnet actuators embedded within the circular chamber of the gaseous damping cushion, two magnetic sensors orthogonally placed within the middle of the gaseous damping cushion, and a printed circuit board for activating the magnetic sensors. The package further comprises a controlling means (not shown) for determining and activating the best magnet with relation to the blood vessel for optimal signal acquisition. The plurality of electromagnet actuators enables a user to control and adjust the magnetic field strength of the magnet individually or collectively so as to produce an optimized signal.

Figure 10:
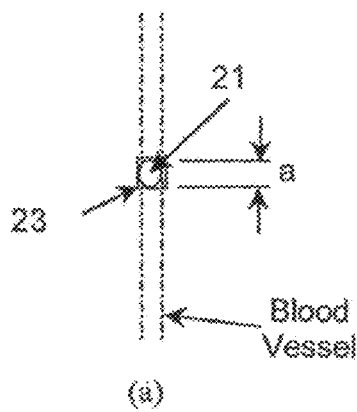
FIGS. 10(a)-(c) illustrate the definitions of the propagation and amplification in the present invention.
Figure 10:
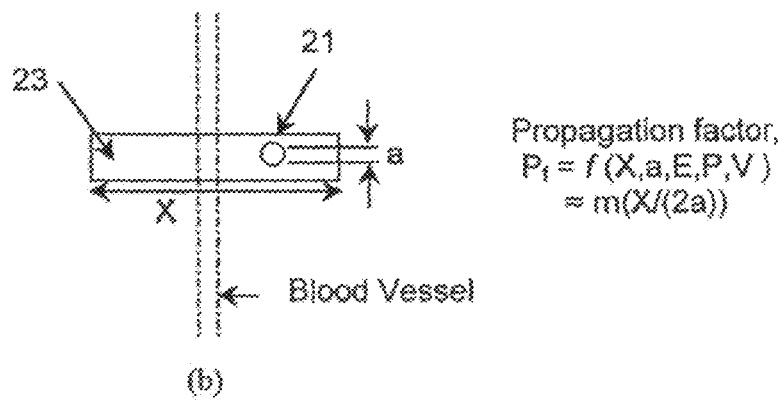
Figure 10:
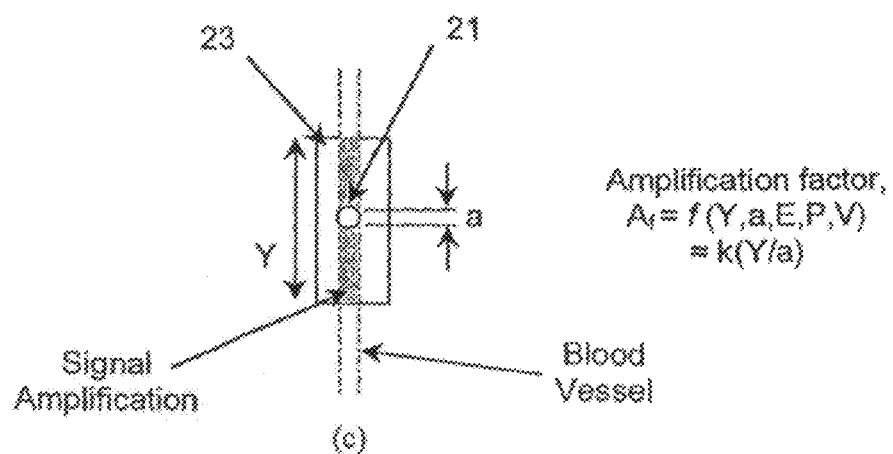

The gaseous damping cushion 23 of the present invention can also amplify and propagate the MMSB. FIGS. 10(a)-(c) illustrate the definitions of the propagation and amplification in the present invention. "a" refers to the characteristic dimension of the magnetic source. The amplification refers to the increase of the magnitude of a variable quantity (e.g., the MMSB signal) caused by the gaseous damping cushion disposed longitudinally along the blood vessel. The propagation refers to the increase of the magnitude of a variable quantity (e.g., the MMSB signal) caused by the gaseous damping cushion disposed cross from the blood vessel. FIG. 10(a) shows the reference MMSB signal acquisition using gaseous damping cushion wherein the gaseous damping cushion has a similar size of the magnet. FIG. 10(b) shows the propagation effect of the gaseous damping cushion for MMSB acquisition. FIG. 10(c) shows the amplification effect of the gaseous damping cushion for MMSB acquisition.

The gaseous damping cushion may be formed from materials with appropriate elasticity (E) such as PTFE. In addition, the cushion will also require a certain amount of pressure (P) and sufficient volume (V) to ensure a good isolation of external noise from interfering with the MMSB.

Figure 11:
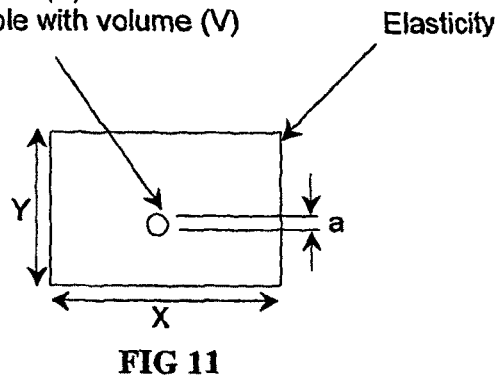
FIG. 11 shows an illustration of the gaseous damping cushion with a freely positioned magnetic source and variables to govern the amplification and propagation results.

Referring to FIG. 11, there is provided an illustration of the gaseous damping cushion with a freely positioned magnetic source and variables to govern the amplification and propagation results. The amplification factor can be calculated according to equation (1):

$$A_f = f(Y, a, E, P, V) \equiv k \frac{Y}{a} \quad (1)$$

wherein $A_f$ is the amplification factor; a is the characteristic dimension of the magnetic source; Y the longitudinal length; E the elasticity of the cushion; P the pressure of the cushion; and V the volume of the cushion; and k the constant for the cushion.

The propagation factor can be calculated according to equation (2):

$$P_f = f(X, a, E, P, V) \equiv m \frac{X}{2a} \quad (2)$$

wherein $P_f$ is the propagation factor; a is the characteristic dimension of the magnetic source; X the latitudinal length; E the elasticity of the cushion; P the pressure of the cushion; and V the volume of the cushion; and m the constant for the cushion.

Table 1 below shows the MMSB signal strength acquired under different mounting configurations. Table 2 below shows the MMSB signal strength with relation to sensor alignment.

TABLE 1

The MMSB signal strength acquired under different mounting configurations

| S/N | Measurement setup | Configuration | Signal Value (mV) | Remark |
|---|---|---|---|---|
| 1 | Baseline signal (without air bubble cushion) | 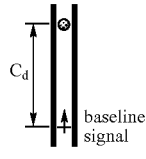 | 1 mV | |
| 2 | Effects of simple cushion | 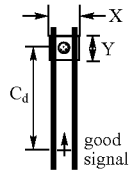 | 10 mV | 10X result improvement with simple cushion |

TABLE 1-continued

The MMSB signal strength acquired under different mounting configurations

| S/N | Measurement setup | Configuration | Signal Value (mV) | Remark |
|---|---|---|---|---|
| 3 | Effects of amplification cushion | 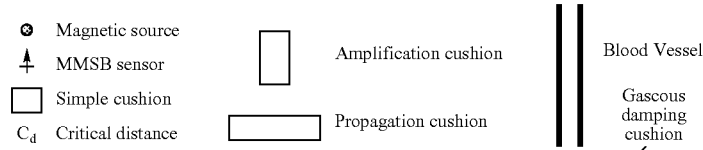 | 40 mV | 40X result improvement with amplification cushion |
| 4 | Effects of propagation cushion | 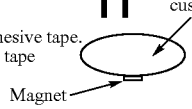 | a) 0 mV<br>b) 8 mV | Propagation effect demonstrated. Results obtained similar to S/N 2 |

Legend

⊗ Magnetic source
⊥ MMSB sensor
☐ Simple cushion
$C_d$ Critical distance
☐ Amplification cushion
☐ Propagation cushion
‖ Blood Vessel
◯ Gaseous damping cushion

*Magnetic source is adhered to measurement site via an adhesive tape.
*Bubble is adhered to the measurement site via an adhesive tape with the magnet placement w.r.t to the bubble as shown.

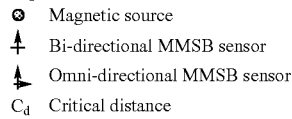

TABLE 2

The MMSB signal strength w.r.t to sensor alignment

| Purpose | Configuration | Signal Value (mV) | Remark |
|---|---|---|---|
| Bi-directional sensor configuration | | a) 20 mV<br>b) 12 mV<br>c) weak signal c) no signal<br>a) best b) good signal signal | Perfect alignment at location a), significant misalignment at b) and extreme misalignment at c). |
| Omni-directional sensor configuration (2 sensors in orthogonal arrangement) | | a) 20 mV<br>b) 18 mV<br>c) best c) 19 mV signal<br>a) best b) best signal signal | Good reading obtained in any alignment. Reading showing normal random fluctuation of ±19 mV. |

Figure 12:
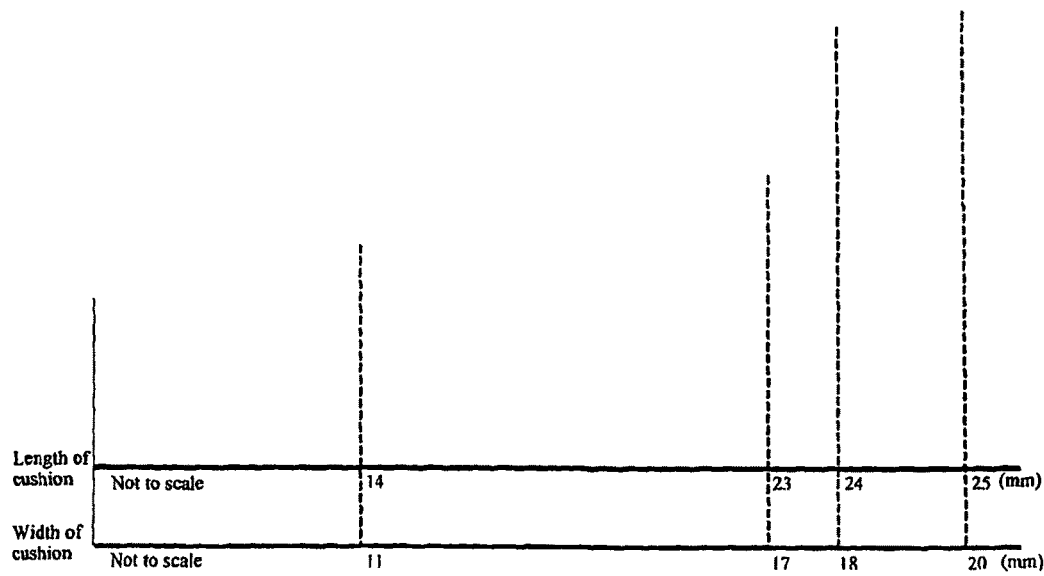
FIG. 12 is a graphic diagram showing the relationship between gaseous damping cushion form factors and MMSB signal values.

Legend
⊗ Magnetic source
⊥ Bi-directional MMSB sensor
⊥ Omni-directional MMSB sensor
$C_d$ Critical distance Referring to FIG. 12, there is provided a graphic diagram showing a typical relationship between gaseous damping cushion form factors and MMSB signal values. The abscissa represents the total volume of the gaseous damping cushion in $mm^3$. The ordinate represents the MMSB signal value output in mV. The results depicted in the graph show the range of values of the volume of the gaseous damping cushion that will result in producing the optimum MMSB signal value acquired. Supplementing the abscissa below are two additional abscissas, length of cushion in mm (not presented to scale) and width of cushion in mm (not presented to scale). They represent typical characteristic dimensions of the length and width of a gaseous damping cushion that produce the corresponding volume.

The packages of the present invention can be assembled by any suitable ways.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A package for an apparatus that non-invasively monitors blood flow of an object, comprising:
    a magnetic source that produces a localized, uni-directional, and constant magnetic field;
    a signal acquisition module with a magnetic sensor, wherein the magnetic sensor is disposed within the localized, uni-directional, and constant magnetic field and detects the modulations of the localized, uni-directional, and constant magnetic field caused by the blood flow in a blood vessel near the skin surface of the object; and
    a gaseous damping cushion, wherein the magnetic source is disposed within or onto the gaseous damping cushion;
    such that the gaseous damping cushion enables the modulations of the localized, uni-directional, and constant magnetic field of the magnetic source caused by the blood flow to be amplified and/or propagated, and isolated from external noises.

2. The package of claim 1, further comprising:
    a signal conditioning module for converting the output of the signal acquisition module with appropriate amplifications; and
    a digital signal processing module for processing the output signal from the signal conditioning module; thereby pulse rate and blood flow anomaly can be monitored.

3. The package of claim 1, further comprising a display/user interface/alarm module for providing visual or acoustic notification to a user.

4. The package of claim 1, wherein the magnetic source is a permanent magnet.

5. The package of claim 1, wherein the magnetic source is an electromagnet.

6. The package of claim 1, wherein the magnetic source comprises a plurality of electromagnets.

7. The package of claim 6, wherein the strength of the localized, uni-directional, and constant magnetic field produced by the plurality of electromagnets is controlled electronically.

8. The package of claim 1, wherein the magnetic sensor is any magnetic sensor with appropriate sensitivity of detecting the modulation of the magnetic field from the magnetic source.

9. The package of claim 8, wherein the magnetic sensor is a giant magnetoresistance (GMR) based magnetic sensor.

10. The package of claim 8, wherein the magnetic sensor is a tunneling magnetoresistive (TMR) magnetic sensor.

11. The package of claim 8, wherein the magnetic sensor is an anisotropic magnetoresistive (AMR) sensor.

12. The package of claim 1, wherein the signal acquisition module comprises a printed circuit board and two magnetic sensors; wherein the printed circuit board is sandwiched by the two magnetic sensors; and wherein the two magnetic sensors have an orthogonal formation.

13. The package of claim 1, wherein the gaseous damping cushion has a doughnut configuration with a circular chamber; wherein the circular chamber is disposed with means for allowing the embedded magnetic source to move and holding the embedded magnetic source in place.

14. The package of claim 13, wherein the means within the circular chamber comprises a plurality of semi-flexible flaps.

15. The package of claim 1, wherein the gaseous damping cushion comprises air or non-magnetic gas.

* * * * *